United States Patent
Uno et al.

(10) Patent No.: US 6,174,500 B1
(45) Date of Patent: Jan. 16, 2001

(54) NEGATIVE ION GENERATING APPARATUS

(75) Inventors: Junichi Uno; Hatsuo Yotsumoto, both of Tokyo (JP)

(73) Assignee: Mitsubishi Denki Kabushiki Kaisha, Tokyo (JP)

( * ) Notice: Under 35 U.S.C. 154(b), the term of this patent shall be extended for 0 days.

(21) Appl. No.: 09/192,238

(22) Filed: Nov. 16, 1998

(30) Foreign Application Priority Data

Jun. 2, 1998 (JP) .................................. 10-153243
Jun. 3, 1998 (JP) .................................. 10-154961

(51) Int. Cl.⁷ .............................. B01J 19/08; B01J 19/12
(52) U.S. Cl. ............................. 422/186.14; 422/186.04
(58) Field of Search ..................... 422/186.04, 186.07, 422/186.14, 186.18, 186.21, 186.08

(56) References Cited

U.S. PATENT DOCUMENTS

| | | | |
|---|---|---|---|
| 3,332,870 | * 7/1967 | Orbach et al. | 422/186.21 |
| 4,657,738 | * 4/1987 | Kanter et al. | 422/186.04 |
| 4,801,435 | * 1/1989 | Tylko | 422/186.04 |
| 5,211,919 | * 5/1993 | Conrad | 422/186.07 |
| 5,766,447 | * 6/1998 | Creijghton | 205/742 |
| 5,858,312 | * 1/1999 | Sindzingre et al. | 422/186.04 |

FOREIGN PATENT DOCUMENTS 195 46 930  12/1995 (DE).

* cited by examiner

*Primary Examiner*—Kathryn Gorgos
*Assistant Examiner*—Wesley A. Nicolas
(74) *Attorney, Agent, or Firm*—Leydig, Voit & Mayer, Ltd.

(57) ABSTRACT

A negative ion generating apparatus includes a ground electrode having a nozzle portion and surrounding a discharge electrode at a position spaced from the ground electrode, a power supply for supplying a negative high voltage to the discharge electrode, a ventilator for drawing air from an inlet and blowing the air between the electrodes. A high voltage induces corona discharges between the electrodes. The ionized negative ion particles produced in the discharge are blown out of an outlet. Alternatively, the ground electrode is a cylinder with a smaller downstream cross-section. The discharge electrode increases the velocity of gas flow and the high speed gas is ionized near the discharge electrode, increasing the rate of generation of negative ion particles. The discharge electrode may include needle electrodes to increase the rate of generation of the negative ion particles.

8 Claims, 8 Drawing Sheets

NEGATIVE ION GENERATING APPARATUS

BACKGROUND OF THE INVENTION

1. Field of the Invention

The present invention relates to a negative ion generating apparatus for generating a high density of negative ion particles, which can be used for the sterilization of foods, drinking water, rooms for living, or for clearing the air in a space. In this specification and claims, the phrase "negative ion" means a gas containing negatively ionized particles.

2. Description of the Prior Art

Various apparatus using active particles, for example, ionized particles or ozone, have been already developed in the prior art, for preventing the propagation of bacteria, cleaning of the air in a space, or for deodorization.

A negative ion generating apparatus takes in oxygen, and other gases into the apparatus, and generates a discharge to ionize the molecules in the gas, by imposing a high voltage, which is called a "corona discharge phenomenon", and produces negatively ionized particles. The gas containing the negatively ionized particles together with ozone gas etc is supplied to a space in which objects are treated by the negatively ionized particles so as to prevent the propagation of bacteria, clean the air therein, deodorize etc.

Figure 9:
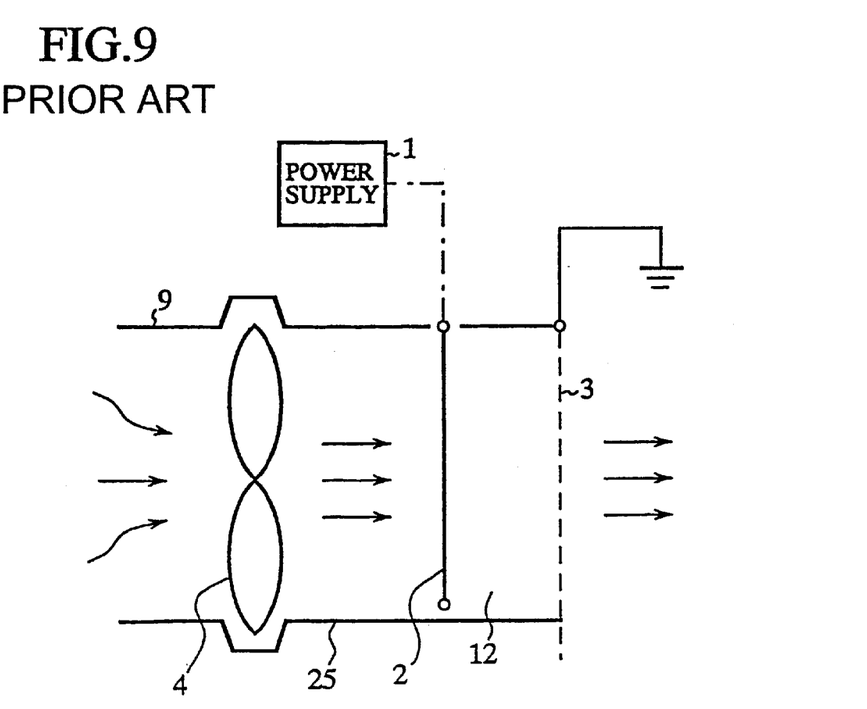
FIG. 9 shows a schematic cross section of a negative ion generating apparatus in the prior art along the flow direction.

FIG. 9 shows a cross sectional view of a negative ion generating apparatus known in the prior art, shown along the direction of the gas flow. The reference numeral 1 denotes a power supply 2 is a discharge electrode comprised of a plurality of parallel thin metal wires, which are electrically connected with the power supply 1. 3 is a ground electrode comprised of metal grid or mesh metal plate, which is arranged to face the discharge electrode. The power supply supplies negative pulses of some kilovolts to the discharge electrode. 4 is a ventilator, for example, an electric fan. 25 is an air passage, through which the air drawn by the ventilator passes. 9 is an air inlet, through which the air is taken in. 12 is a discharge space or discharge chamber between the discharge electrode 2 and ground electrode 3, in which the air is ionized. The ionized gas containing negative ion particles passes through the grid or mesh plate of the ground electrode 3, to be radiated on the objects to be sterilized and so on. In this specification and claims, the space or the chamber, in which such objects to be sterilized are disposed, is called an "object space".

The functioning of the negative ion generating apparatus of the prior art is explained below.

The ventilator (electric fan) 4 takes in a gas, preferably air, from the exterior space into the apparatus, and urges the gas to move towards the object space through the discharge electrode 2 and ground electrode 3. Hence a gas flow arises in the apparatus from the upstream to the downstream direction. Negative pulses of some kilovolts are supplied to the thin wires of the discharge electrode 2 from the power supply 1. This causes a corona discharge between the negatively charged discharge electrode 2 and the ground electrode 3. It is understood, in general, that there is only one discharge point in the thin wires, for every one pulse where the corona discharge occurs, such point being called a "corona discharge point".

In a corona discharging area, electrons combine with gas particles (especially with oxygen molecules), which are found near to the discharge electrode 2, to generate negative ion particles. Simultaneously, a small quantity of ozone can be generated, as a result of collision and dissociation of negative ionized particles, which are originated from the oxygen molecules. The gas containing the negative ion particles, which are generated at an area near to the discharge electrode 2, in such a manner, is driven to flow into the object space, which is found in the downstream area, after passing through the grid wires or a mesh plate of the ground electrode, by the blowing force of the ventilator ( for example, an electric fan). The negative ions can be used for preventing the propagation of the bacteria, for example.

In another expression, the ventilator 4 sucks the air from the exterior through the inlet 9, and the air is sent to the discharge space 12 through the air passage 25. A high voltage from the power supply 1 is imposed on the discharge electrode 2, which causes corona discharges in the discharge space 12 between the ground electrode 3 and the discharge electrode. The negatively ionized particles, for example, $O^{2-}$ particles, generated in the corona discharges move towards the ground electrode 3. The ionized gas is blown out from the electrode portion towards the exterior of the apparatus, by the blowing force of the ventilator 4.

As shown in FIG. 9, the discharge chamber 12 in the prior art that the air flows through has a constant cross section in its whole region from upstream to downstream. Thus, when the capacity of the electric fan 1 is constant, the flow velocity is constant. As a result, the generating rate of negative ion particles per unit time and the supplying rate of negative ion particles per unit time are constant.

Figure 10:
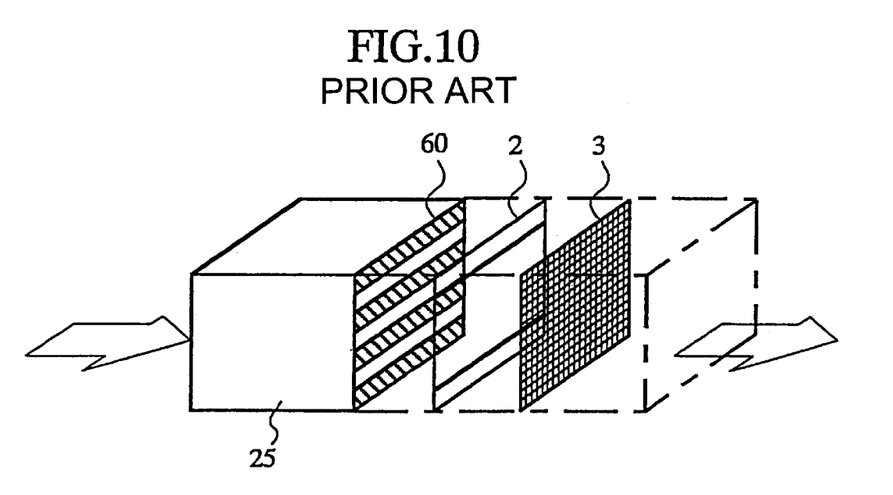
FIG. 10 shows a schematic perspective view of the electrodes region of a negative ion generating apparatus having a gas flow direction control member.

A gas flow direction deflecting board 6, as shown in FIG. 10, is disclosed in the prior art, for controlling the flow direction, and for increasing the negative ion particle generating rate per unit time, by increasing the flow velocity at the area near to the discharge electrode.

In the negative ion generating apparatus in the prior art having such a structure, a large portion of the generated negative ion particles tend to move towards the grid wires or mesh plate of the ground electrode 3 and to be absorbed therein, because of their negative charges. Consequently, there is a problem that only a small number of the negative ions can pass through the grid wires or mesh plate.

In the negative ion generating apparatus of the prior art, the supplying capacity of the negative ion particles to the object space, after their generation in the region near to the discharge electrode, is determined by the capacity of an electric fan. Thus, an augmentation of the fan capacity is required to increase the density of the negative ion particles in the object space, which leads, in turn, to the problem of the increase of the electric power consumption.

Although the flow direction control member, as shown in the prior art, is effective regarding of the control of the flow direction and the speeding up of the air flow, it entails the problems that the flow direction control member, which is perpendicular to the flow direction, causes a loss of pressure head of the air flow. Additionally, the flow direction control member shall be arranged at an upstream position of the discharge electrode, spaced some distance, for avoiding the blunting of the electric field by it. Thus, even if the velocity of the flow is increased by the member, the velocity is decreased at the region of the discharge electrode, when it arrives there. Consequently, there is a problem that the negative ion particles can not be generated effectively. Another problem is that the number of member parts of the apparatus increases, and the size of the apparatus further becomes large.

Moreover, there is a requirement regarding environmental standards which requires that the density of ozone simultaneously generated together with the negative ion particles shall be under 0.1 ppm.

The negative ion generating apparatus in the prior art has further drawbacks as follows:

The discharge electrode is comprised of thin wires disposed in parallel, thus there is a limitation in the number of the electrodes disposable in an unit area, avoiding interference between the discharge electrodes. On the other hand, the number of the electrodes corresponds to the number of corona discharges per unit area.

The thin wires, which are pulled from both sides, have a tendency to easily break due to the high voltage applied thereon.

The direction of the corona discharges is substantially parallel to the flow direction of the gas, thus, the generated negative ion particles, are easily caught by the ground electrode, which is a mesh plate.

Thus the supply efficiency of the generated negative ion particles into the object space is small.

Finally, the size of the apparatus is large.

The present invention eliminates the drawbacks of the negative ion generating apparatus of the prior art.

SUMMARY OF THE INVENTION

An objet of the present invention is to propose a negative ion generating apparatus, which can generate effectively high density negative ion particles.

Another object of the present invention is to propose a negative ion generating apparatus, which can supply increased number of negative ion particles per unit time into the object space, without increasing the electric power consumption.

Another object of the present invention is to propose a negative ion generating apparatus, which can generate increased number of negative ion particles per unit time.

Further another object of the present invention is to propose a negative ion generating apparatus, which occupies a small space, and which can be fabricated using a small number of element parts.

Namely, the object of the present invention is attained by a negative ion generating apparatus comprising:
- a first electrode;
- a second electrode disposed at a position spaced at a predetermined distance from the first electrode;
- a ventilator, which sucks in a gas from a gas inlet and sends it into a space between the first electrode and the second electrode to generate a gas flow;
- a power supply to apply a voltage between the first electrode and the second electrode to induce corona discharges between them;
- an outlet opening for negative ion particles which are generated by the corona discharges in the gas sent between the first and the second electrodes;
- characterized in that the first electrode and/or the outlet opening is formed as a nozzle to narrow the gas passage and to increase the velocity of the gas flow.

In an embodiment, the first electrode is formed as a surrounding body surrounding the second electrode, and the nozzle is comprised of a tapered off cone like portion or a curved portion of the first electrode.

In another embodiment, the tapered off cone like portion or the curved portion is comprised of a pair of surfaces arranged along the gas flow direction and are facing to each other from the both sides of the gas flow.

In another embodiment, a duct is disposed between the inlet and the first electrode, and the downstream portion of the duct is formed as a nozzle.

In another embodiment, the outlet opening of the negative ion particles is comprised of a hole disposed in a electrically insulating member, which is connected to the downstream portion of the first electrode.

In another embodiment, the outlet opening disposed in the electrically insulating member is formed as a blowing out nozzle.

In another embodiment, an adjusting damper for narrowing the gas passage is disposed as a nozzle in the reaction chamber, where the corona discharges occur, an end of the adjusting damper is rotatably connected to the inner surface of the reaction chamber, and the other end is freely rotatable, the adjusting damper is urged by a spring in the direction to narrow the gas passage for controlling the velocity of the gas flow, the first electrode is arranged adjacently to the other end of the adjusting plate, and the second electrode is arranged at a downstream of the first electrode.

In another embodiment, the adjusting damper is comprised of a pair of dampers arranged along the gas flow, facing each other from both sides of the gas flow.

In another embodiment, the apparatus comprises an object chamber, in which objects to be exposed in the negative ion particles are disposed. The object chamber is connected through the outlet opening with the negative ion generating portion, and a negative ion particle density sensor is arranged in the object chamber, which detects the density of the negative ion particles, which are supplied together with the ozone gas into the object chamber, and sends a negative ion particles density control signal to the ventilator, the ventilator controls the flow rate, based on the negative ion particles density signal.

In another embodiment, the apparatus comprises an object chamber, in which objects to be exposed in the negative ion particles are disposed. The object chamber is connected through the outlet opening with the negative ion generating apparatus, an ozone density sensor is arranged in the object chamber, which detects the density of the ozone gas, which is supplied together with the negative ion particles into the object chamber, and a discharge controller, which receives an ozone density control signal from the ozone density sensor and controls the ozone density, based on the ozone density signal.

In another embodiment, the first electrode has a substantially cylindrical portion, through which the flowing gas passes, and an outlet opening of the gas, thereby, the cross section of the outlet opening at the upstream portion is larger than that of the downstream portion, so that the outlet opening functions as a nozzle.

In an embodiment, the second electrode is substantially parallel with the plane of the outlet opening, and is disposed in the outlet opening at the downstream portion or at the most downstream portion of the outlet opening.

In an embodiment, the cross section of the second electrode increases gradually from its most upstream portion to its most downstream portion.

In an embodiment, the form of the outlet opening is substantially a circle, and the second electrode has a plurality of needle formed electrodes, which are disposed in the plane of the first electrode and are projecting in the radial direction.

In an embodiment, the plurality of the needle formed electrodes are arranged in the plane of the outlet opening equidistantly in the angular direction.

In an embodiment, the plurality of the needle formed electrodes extend from a supporting member, which is made from electrically insulating material.

In an embodiment, the transverse cross section of the supporting member is circle.

In an embodiment, the transverse cross section of the supporting member at a downstream portion is larger than that of an upstream portion.

In an embodiment, the first electrode is maintained at the ground voltage, and the second electrode is electrically connected with a power supply, which generates negative voltage pulses.

Namely, the object of the present invention is attained also by a negative ion generating apparatus comprising:

a first electrode;

a second electrode disposed at a position spaced at a predetermined distance from the first electrode;

a ventilator, which sucks in gas from a gas inlet and sends it into the space between the first electrode and the second electrode to generate a gas flow;

a power supply to supply a negative voltage between the first electrode and the second electrode to induce corona discharges between them;

an outlet opening of negative ion particles, which are generated by the corona discharges in the gas between the first and the second electrodes;

characterized in that the form of the outlet opening is substantially a circle, and the second electrode has a plurality of needle formed electrodes, which are disposed in the plane of the first electrode and are projecting in the radial direction.

DETAILED DESCRIPTION OF THE PREFERRED EMBODIMENTS

Preferred embodiments of the present invention are explained below.

First Embodiment

In this embodiment the discharge electrode (second electrode) is formed as a surrounding body, which has the form of a nozzle narrowing the flow passage so as to increase the velocity of the gas flow.

Figure 1A:
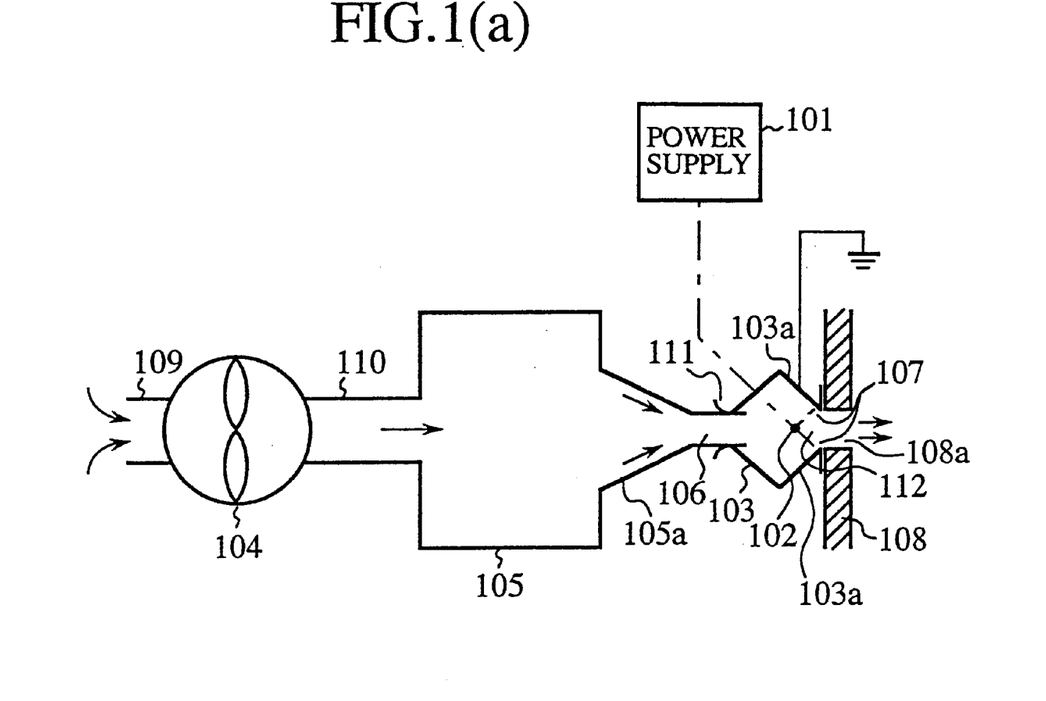
FIG. 1(a) shows a schematic cross section of the first embodiment of a negative ion generating apparatus according to the present invention along the flow direction.
Figure 1B:
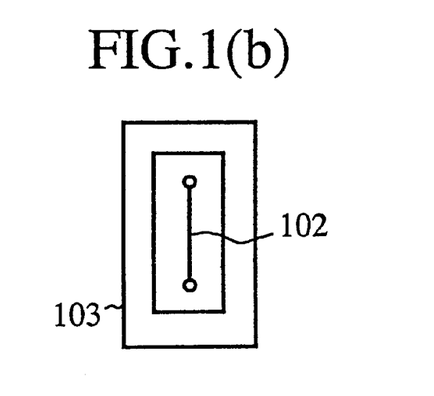
FIG. 1(b), shows the second electrode viewed in the flow direction.

FIG. 1(a) shows a cross section of the first embodiment of a negative ion generating apparatus according to the present invention along the direction of the gas flow, and FIG. 1(b) shows a schematic cross section of the apparatus at the discharge electrode region in a plane perpendicular to the gas flow direction.

Reference numeral 101 denotes a power supply, 102 is a discharge electrode (second electrode ) made from thin tungsten wires, which are connected with the power supply 101, 103 is a ground electrode, formed as a nozzle, 104 is a fan or a blower as a ventilator, 105 is a duct for homogenizing the flow velocity in a plane perpendicular to the flow direction, 106 is a nozzle, 107 is a discharge surface, 108 is a blowing out nozzle made from an electrically insulating material, for example, vinyl chloride, 109 is an inlet of gas for taking in the air from the outside, 110 is a gas passage for sending the gas flow from the ventilator 104 to the duct 105, 111 is an insulating member arranged between the nozzle 106 and the ground electrode (first electrode) 103 for insulating them from each other, which is made from an electrically insulating material, for example, a rubber material, 112 is a discharge space in which the gas discharges and dissociates into a negative ion, for example, $O^{2-}$. As to the material of the duct 105, any electrically conductive material or any electrically insulating material, for example, vinyl chloride, is applicable.

The ground electrode (first electrode) 103 is a surrounding body, as shown in FIG. 1(a). More specifically, it is a hollow body having a rectangular transverse cross section. It has a pair of tapered off, i.e., conical, portions, the spacing between them is large at a middle portion along the gas flow direction, and they approach to each other at the region adjacent to the blow out nozzle 108, which is made from electrically insulating material. The surrounding body has an inlet at its upstream portion, through which a gas flow from the nozzle 106 is supplied. It has an outlet opening in its downstream portion which is connected with the blow out nozzle 108. The blow out nozzle 108 is made from insulating material. The discharge electrode 102 is disposed at a downstream portion of the interior of surrounding body as a ground electrode 103, spacing a certain distance from the ground electrode 103.

The transverse cross section of this ground electrode 103 is a hollow rectangular, with a height of 60 mm, width of 10 mm, as shown in FIG. 1(b). Due to this structure, discharges occur at two regions in the downstream portion of the ground electrode, namely at the region between the upper portion of the outlet opening and the discharge electrode, and the region between the lower portion of the outlet opening and the discharge electrode.

The function of the first embodiment is explained below.

The ventilator 104 takes in the external air through the gas inlet 109. The air accelerated by the ventilator 104 is sent to the duct 105 for homogenizing the velocity distribution in a plane perpendicular to the flow direction. The cross section of the gas flow is narrowed by the nozzle 105a, which has a tapered off shape, and the gas flow reaches a high velocity. The gas flow passes an area between the discharge electrode 102 and the ground electrode 103 formed as a nozzle, then goes out from the blown out nozzle 108, which is made from electrically insulating material. When a high voltage, for example, 8 KV, is imposed between the discharge electrode 102 and the ground electrode 102 by the power supply 101, corona discharges occur between the discharge electrode 102 and the ground electrode 103. Negative ion particles, which are ionized in the corona discharges, are blown out together with the gas flow from the ground electrode 103. The negative ion particles have the same high speed as the gas flow.

The corona discharges occur at two regions, namely at the upper portion and the lower portion of the ground electrode 103, thus the negative ion generating rate is higher compared with the prior art.

As explained above, in the first embodiment, the gas flow is accelerated as a whole by the ground electrode formed as a nozzle. And the negative ion particles generated in the discharge space 112 between the discharge electrode 102 and the ground electrode 103 are blown out to the exterior of the apparatus with a high speed gas flow. Consequently, the proportion of the negative ion particles, which are caught by the ground electrode 103, etc, to the number of the generated negative ion particles decreases compared with the prior art, so the loss of the negative ion particles is small. This leads to an improvement of the negative ion supplying efficiency, Further, the negative ion particles are generated at two discharge surfaces 107, namely at a pair of tapered surfaces, which are facing each other, as explained above. As result, the generation rate of the negative ion particles is larger than a prior art.

When the material of the electrically insulating blow out nozzle 108 is selected from materials which can prevent the generation of the static electricity, the final generating efficiency of the negative ion particles may be further improved.

Second Embodiment

Figure 2A:
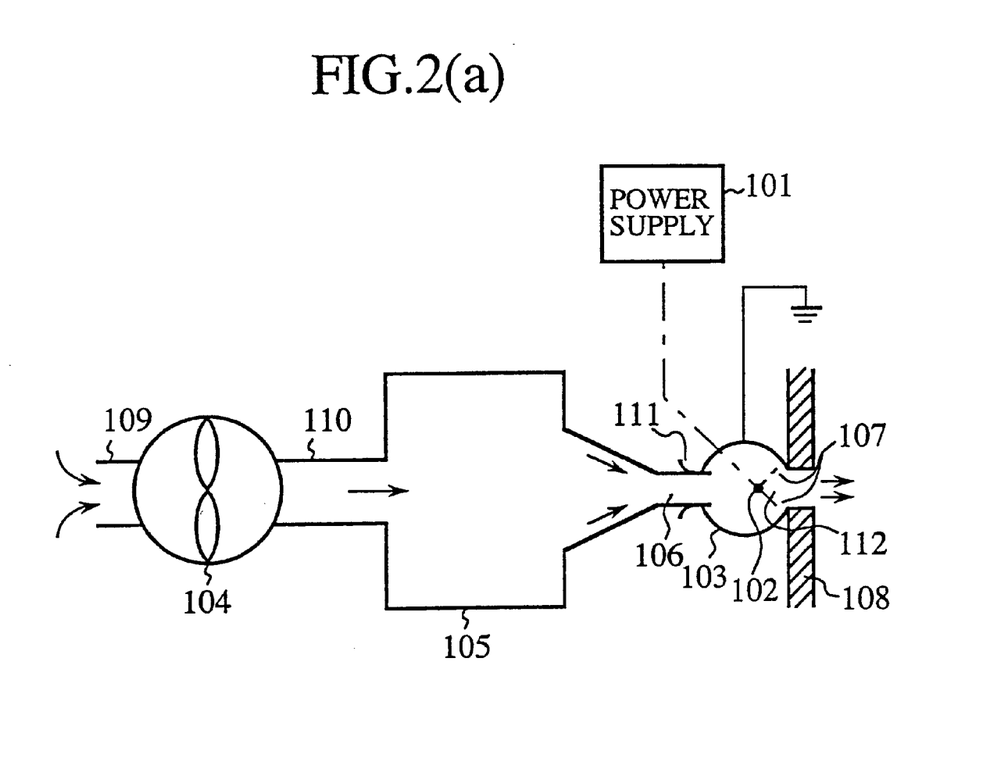
FIG. 2(a) shows a schematic cross section of the second embodiment of a negative ion generating apparatus according to the present invention along the flow direction.
Figure 2B:
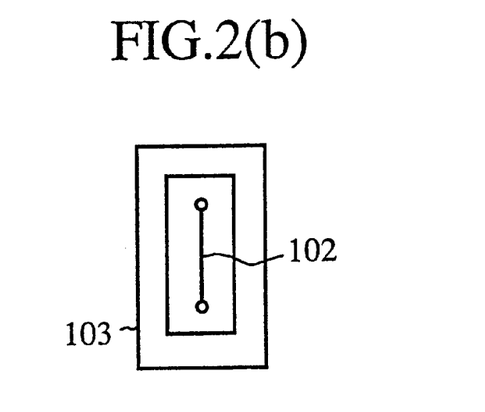
FIG. 2(b) shows the second electrode viewed in the flow direction.

In the first embodiment, the ground electrode 103 is formed as a tapered off nozzle, the transverse cross section of which is rectangular. The transverse cross section of the ground electrode in the second embodiment is, however, a circle, as shown in FIGS. 2(a), and 2(b). This embodiment has same effects as the effects of the first embodiment.

Third embodiment

Figure 3A:
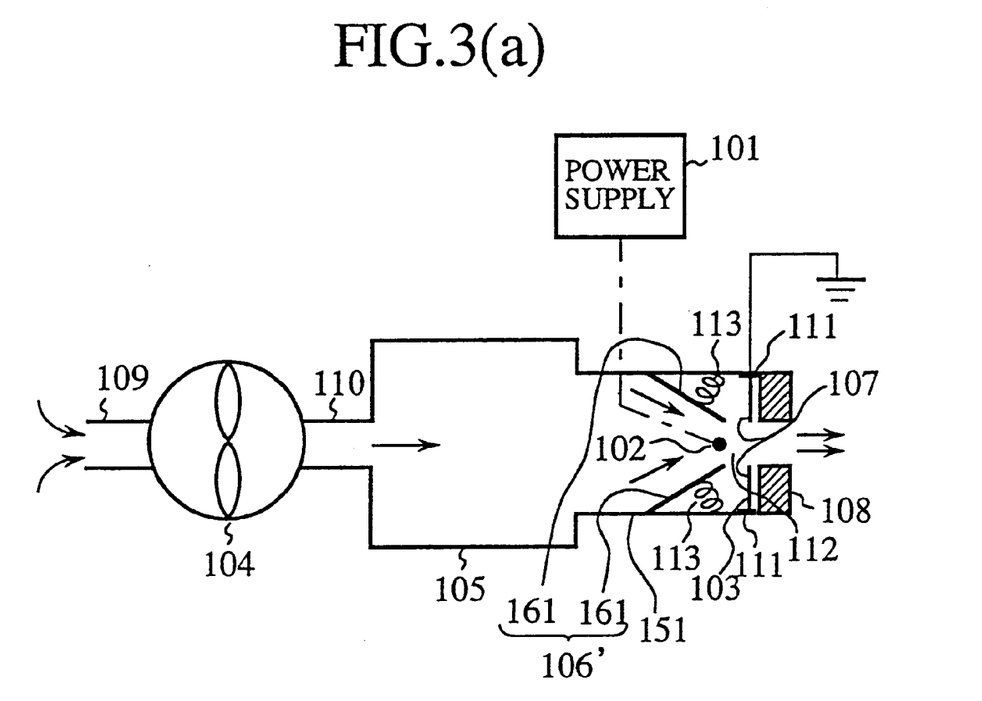
FIG. 3(a) shows a schematic cross section of the third embodiment of a negative ion generating apparatus according to the present invention along the flow direction.
Figure 3B:
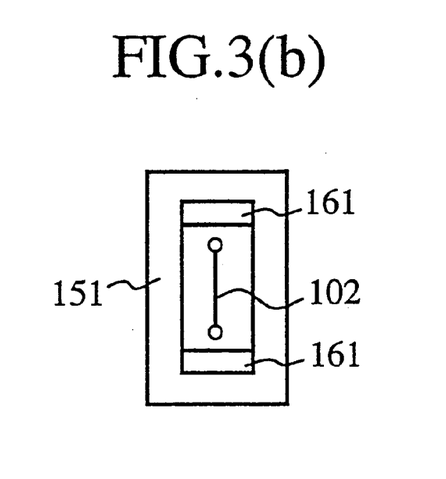
FIG. 3(b) shows the second electrode viewed in the flow direction.
Figure 3C:
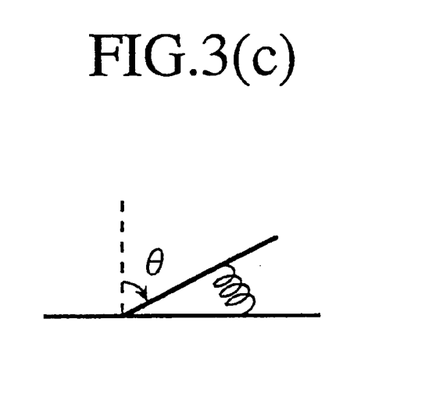
FIG. 3(c) shows a schematic cross section of an adjusting damper.

FIG. 3(a) shows a schematic cross section of the third embodiment of a negative ion generating apparatus according to the present invention along the flow direction, FIG. 3(b) shows the second electrode region viewed in the flow direction, and FIG. 3(c) shows a schematic cross section of an adjusting damper.

The reference numeral 101 is a power supply, 102 is a discharge electrode (second electrode), 103 is a ground electrode (first electrode), 104 is a ventilator, 105 is a duct, 151 is a reaction chamber, 106' is an adjusting nozzle, which is comprised of a pair of adjusting dampers 161 facing each other at opposite sides of the gas flow axis. The angle of the adjusting damper in respect to a plane perpendicular to the gas flow direction, the nozzle angle θ, is adjusted by the adjusting dampers. 107 is a discharge surface, 108 is an insulating blow out nozzle, 109 is an inlet of gas, 110 is a gas passage, 111 is an insulating member made from, for example, gum, 112 is a discharge space, 113 is an urging member, for example, a spring.

An end of the adjusting damper 161 is connected with the inner surface of the reaction chamber 151 using, for example hinges, so as to be rotatable, and the other end is a free end. The backside of the adjusting dampers 161 is urged by the urging member, for example, a spring, so as to increase the velocity of the gas flow, by narrowing the cross section of the gas passage, as a choke functions.

The function of the third embodiment is explained below.

The gas flow accelerated by the ventilator 104 is supplied into the reaction chamber 151 through the duct 105. The velocity distribution of the gas flow in a plane perpendicular to the flow direction is homogenized in the duct. The adjusting nozzle 106' is urged by the gas flow, depending on the force of the gas flow. On the other hand, the adjusting damper 161 is urged also by the urging member 113 in the opposite direction. Thus the nozzle angle is automatically controlled, depending upon the force of the gas flow. When the force of the gas flow is large, the nozzle angle is large, when the force of the gas flow is small, the nozzle angle is small. In this manner, a high velocity of the gas flow between the discharge electrode 102 and the ground electrode 103 can be assured. When a high voltage is imposed between the discharge electrode 102 and the nozzle formed ground electrode 103 from the power supply 102, corona discharges occur between them. The negative ion particles generated in the discharge space 112 between the electrodes are blown out through the insulating blowing out nozzle 108 at high speed together with the gas flow. Because the discharges occur at two discharge surfaces, namely at the upper region and the lower region of the gas flow, the generating rate of the negative ion particles is large.

According to this embodiment, the velocity of the gas flow can be maintained at a constant level, due to the function of the adjusting damper. So, it is possible to make constant the generating rate of the negative ion particles, independently from the quantity of the gas flow from the gas flow accelerating ventilator 104. As a result, the stable provision of high density negative ion particles can be realized. As mentioned above, the generating rate of the negative ion particles is large, because there are two discharge surfaces 107.

Fourth Embodiment

Figure 4:
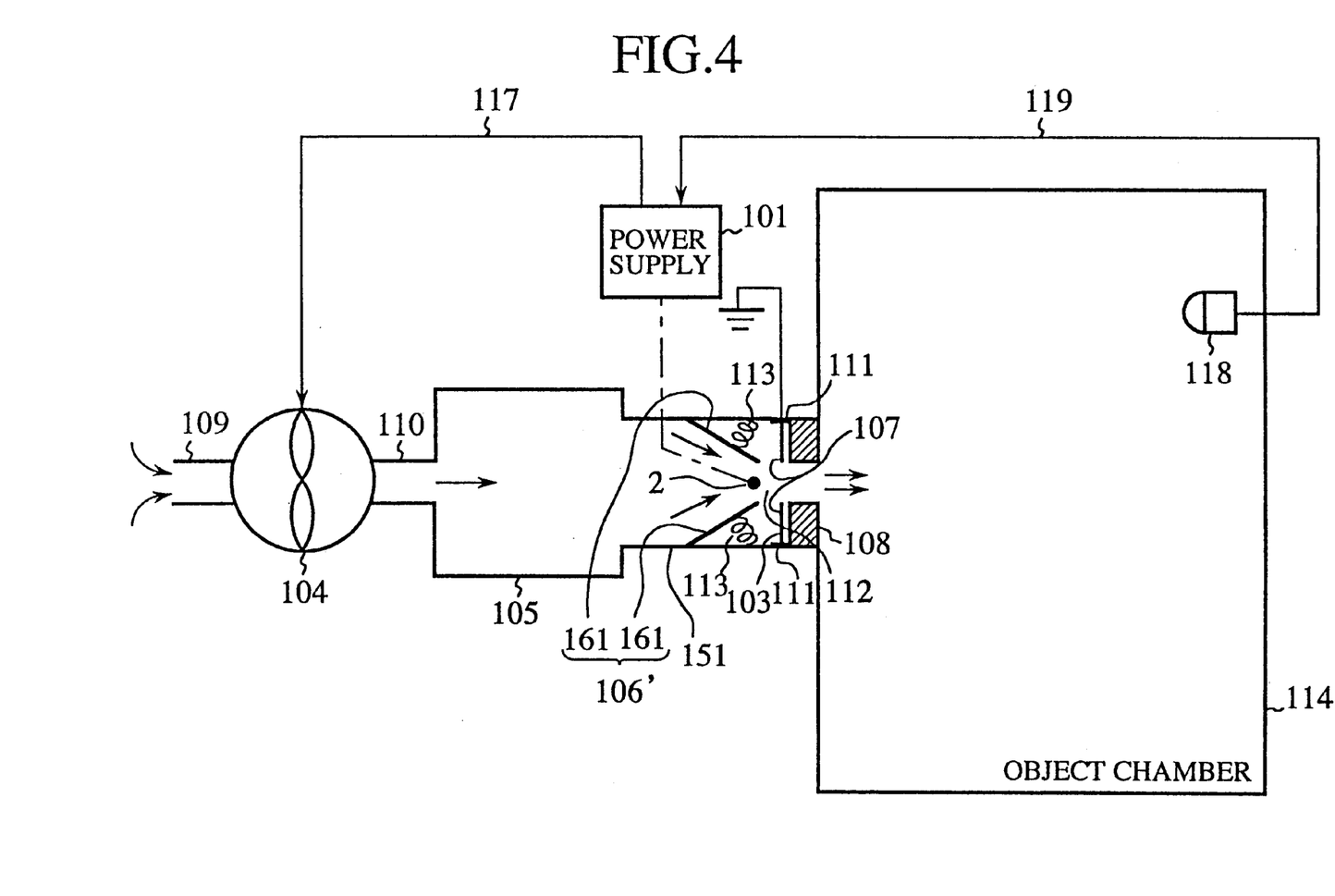
FIG. 4 shows a schematic cross section of the fourth embodiment of a negative ion generating apparatus according to the present invention along the flow direction.

FIG. 4 shows a schematic cross section of the fourth embodiment of a negative ion generating apparatus, according to the present invention, along the flow direction.

Reference numeral 101 denotes a power supply, 102 is a discharge electrode electrically connected with the power supply 101, 103 is a ground electrode disposed at a downstream of the discharge electrode 102, 104 is a ventilator, for example, a blower or a fan, 105 is a duct for homogenizing the velocity distribution in a plane perpendicular to the flow direction, 151 is a reaction chamber, 106' is an adjusting nozzle, which is comprised of a pair of adjusting dampers 161 facing each other at opposite sides of the gas flow axis, for adjusting the nozzle angle θ. 107 is a discharge surface, 108 is an insulating blow out nozzle, which is made from, for example, vinyl chloride, 109 is an inlet of gas for taking in the exterior air to the ventilator, 110 is a gas passage, 111 is an insulating member, which is made from, for example, gum, 112 is the discharge space, 113 is an urging member, for example, a spring.

114 is an object chamber, in which objects to be exposed in the negative ion particles can be disposed, 118 is a sensor for detecting the density of the negative ion particles in the ionized gas, 119 is the negative ion density signal from the sensor 118, 117 is a signal from a controller incorporated in the power supply 101, for controlling the ventilator to control the flow rate of the gas flow, depending on the negative ion density signal 119. A container for vegetables, a special chamber for human beings, for example, an operating room, can be raised as examples of the object chamber. As examples of objects to be exposed in the negative ion particles, the merchandises, for example, vegetables and the interiors or the inner surfaces of room can be raised.

The function of the fourth embodiment is explained below.

The gas flow from the ventilator 104 is supplied through the duct 105. In a same manner as in the third embodiment, the adjusting nozzle 106' controls automatically the nozzle angle, depending on the force of the gas flow, so that a high velocity of the gas flow is obtained between the discharge electrode 102 and the ground electrode 103. When a high voltage is imposed between the discharge electrode 102 and the ground electrode 103 from the power supply 101, an ionized gas containing negative ion particles and ozone gas is generated between the electrodes, and the ionized gas is blown out through the insulating blowing out nozzle 108 at high speed.

For regulating the density of the negative ion particles in an appropriate region, a sensor 118 for detecting the density of negative ion particles is disposed in the object chamber 114. The output signal 119 is sent to a control circuit (not shown) incorporated in the power supply 101, which processes it. The control signal 117, the output of the control circuit, controls the rotation rate of the ventilator 104 so as to control the flow rate of the gas flow. The density of the negative ion particles depends upon the flow rate of the gas flow. Thus, the density of the negative ion particles can be controlled by controlling the flow rate.

When the flow rate is small, the force of the gas flow is weak, thus the nozzle angle of the adjusting damper 161 becomes small. On the contrary, when the force of gas flow is strong, the nozzle angle becomes large. As a result, the velocity of the gas flow between the discharge electrode 102 and the ground electrode 103 is maintained to be constant. Consequently, the generating rate of the negative ion particles is substantially stable.

As explained above, according to the fourth embodiment, the control circuit incorporated in the power supply 101 generates a control signal 117, which controls the ventilator 104 to control the rotation rate for controlling the flow rate, based on the output signal of the sensor 118 for detecting the density of the negative ion particles, which is disposed in the object chamber 114. Thus, the density of the negative ion particles in the ionized gas can be controlled. In addition, the velocity of the gas flow between the ground electrode 103 and the discharge electrode 102 is maintained to be constant, by an automatic movement of the adjusting damper 161, which is a component of the adjusting nozzle 106', independently from the flow rate of the gas flow. As a result, the density of the negative ion particles is assured to be in a level sufficient for practical use.

Fifth Embodiment

Figure 5:
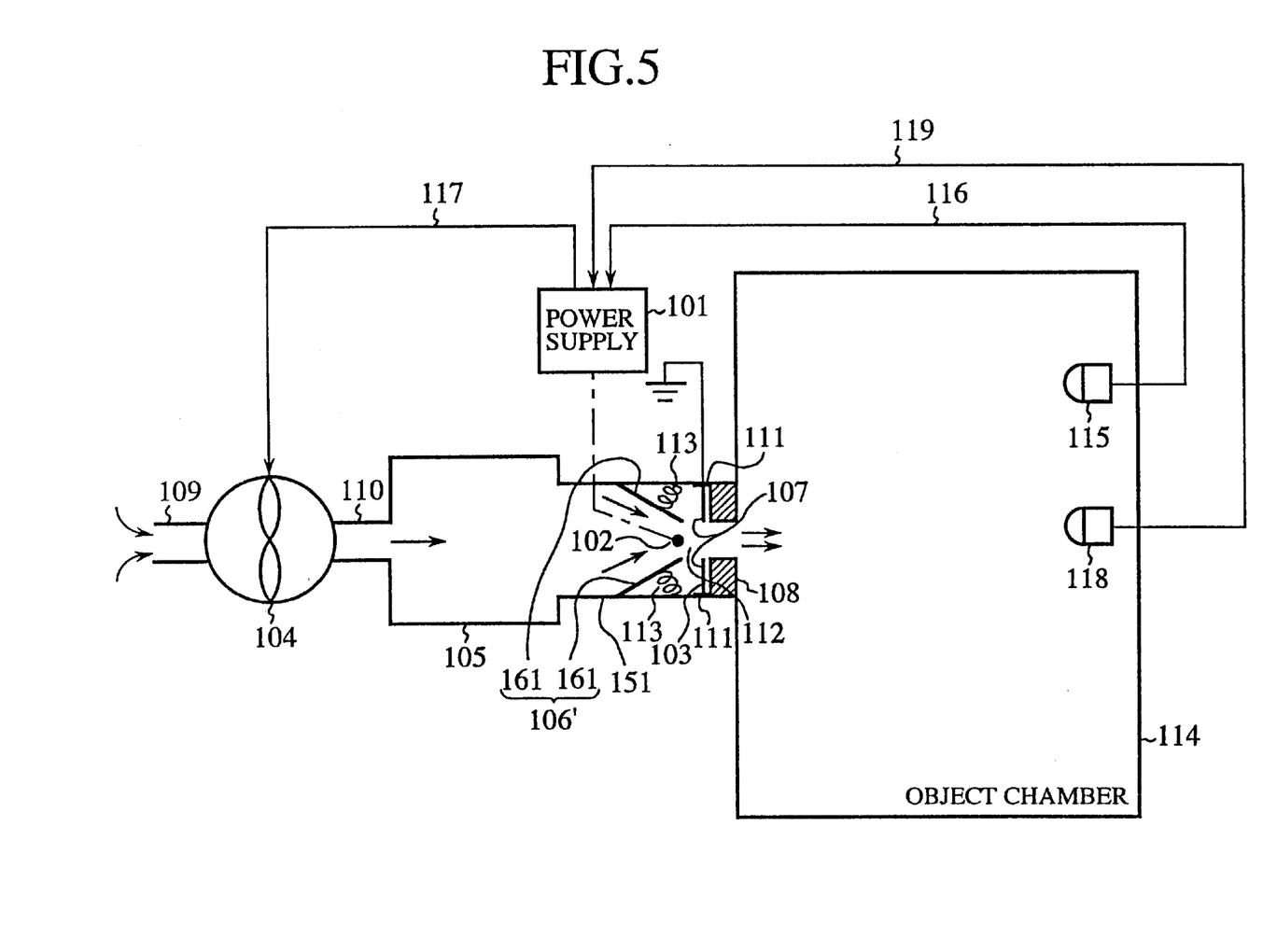
FIG. 5 shows a schematic cross section of the fifth embodiment of a negative ion generating apparatus according to the present invention along the flow direction.

FIG. 5 shows a schematic cross section of the fifth embodiment of a negative ion generating apparatus, according to the present invention, along the flow direction.

Reference numeral 101 denotes a power supply, 102 is a discharge electrode electrically connected with the power supply 101, 103 is a ground electrode disposed downstream of the discharge electrode 102, 104 is a ventilator, for example, a blower or a fan, 105 is a duct for homogenizing the velocity distribution in a plane perpendicular to the flow direction, 151 is a reaction chamber, 106' is an adjusting nozzle, which is comprised of a pair of adjusting dampers 161 facing to each other at the both sides of the gas flow axis, for adjusting the nozzle angle θ, 107 is a discharge surface, 108 is an insulating blow out nozzle, which is made from, for example, vinyl chloride, 109 is an inlet of gas for taking in the exterior air towards the ventilator, 110 is a gas passage, 111 is an insulating member, which is made from, for example, gum, 112 is the discharge space, 113 is an urging member, for example, a spring.

114 is an object chamber, in which objects to be exposed in the negative ion particles can be disposed. 115 is a sensor for detecting the density of ozone in the ionized gas, 116 is the ozone density signal from the sensor 115, for controlling the frequency controller (not shown) incorporated in the power supply 101.

A container for vegetables, a special chamber for human beings, for example, an operating room, can be raised as examples of the object chamber. As examples of the object to be exposed in the negative ion particles, the merchandises, for example, vegetables and the interiors or the inner surfaces of a room can be raised.

The function of the fifth embodiment is explained below.

The gas flow from the ventilator 104 is supplied through the duct 105. The adjusting nozzle 106' controls automatically the nozzle angle, depending on the force of the gas flow, so that a high velocity of the gas flow is obtained between the discharge electrode 102 and the ground electrode 103. When a high voltage is imposed between the discharge electrode 102 and the ground electrode 103 from the power supply 101, an ionized gas containing negative ion particles and ozone gas is generated, and it is blown out through the insulating blowing out nozzle 108 at high speed.

For regulating the density of ozone, a sensor 115 for detecting the density of ozone is disposed in the object chamber 114. The output signal 116 of the sensor controls a frequency controller (not shown) incorporated in the power supply 101. The generation rate of ozone can be controlled by the discharge frequency. Thus, the density of ozone can be controlled by this control.

When the flow rate becomes small, the force of the gas flow becomes weak, and the nozzle angle of the adjusting damper 161 is reduced, due to the urging force of the urging member 113. On the contrary, when the force of gas flow becomes strong, the nozzle angle is increased. As a result, the velocity of the gas flow between the discharge electrode 102 and the ground electrode 103 is maintained constant. Consequently, the generating rate of the negative ion particles is substantially stable.

As explained above, according to the fifth embodiment, the frequency controller incorporated in the power supply 101 is controlled, based on the output of the sensor 115 for detecting the density of ozone disposed in the object chamber 114. The density of ozone in the ionized gas can be regulated, in this way, so as to comply with the environmental requirement. In addition, the velocity of the gas flow between the ground electrode 103 and the discharge electrode 102 is maintained constant, by the automatic movement of the adjusting damper 161, which is a component of the adjusting nozzle 106', independently from the flow rate of the gas flow. As a result, the density of the negative ion particles is assured to be in a level sufficient for a practical use.

Sixth embodiment

The ground electrode in the sixth embodiment is formed as a cylinder, and the outlet opening is formed as a nozzle for narrowing the gas passage.

Figure 6A:
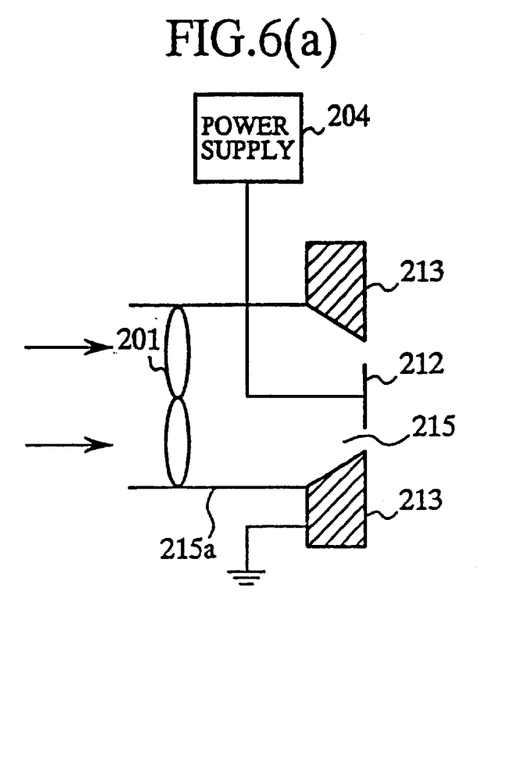
FIG. 6(a) shows a schematic cross section of the sixth embodiment of a negative ion generating apparatus according to the present invention along the flow direction.

FIG. 6(a) shows a schematic cross section of the sixth embodiment of a negative ion generating apparatus according to the present invention along the flow direction.

Reference numeral 201 denotes a fan (ventilator), 212 is a discharge electrode (second electrode), 213 is a ground electrode (first electrode) formed as a cylinder surrounding the discharge electrode 212, 204 is a power supply for supplying negative voltage pulses of some KV to the discharge electrode, 215 is an outlet opening disposed in the ground electrode 213, which is a through hole in the direction of the ground electrode axis.

Figure 6B:
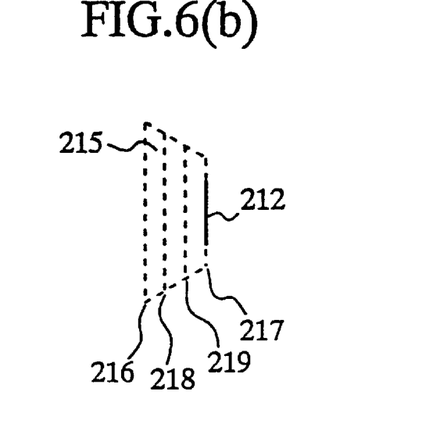
FIG. 6(b) shows a detailed cross section of the outlet opening portion of the apparatus of FIG. 6(a).

FIG. 6(b) shows a detailed figure of FIG. 6(a), for explanation of the configuration of the discharge electrode 212 in the outlet opening 215. In the figure, the most upstream position 216, the most downstream position 217, and arbitrary intermediate first position 218, second position 219 between them are indicated. The diameter at the second position 219 of the outlet opening 215 is smaller than that of at the first position 218. The figure shows an example that the discharge electrode 212 is disposed in the outlet opening 215, being in a row with the plane of the most downstream position 217. In other words, the discharge electrode 212 is configured to be parallel with the plane of the ground electrode 213 (first electrode) and is positioned at the most downstream position 217 of the outlet opening.

The function of the sixth embodiment is explained below.

External gas (preferably air) is taken in into the apparatus by the fan 201. The gas from the external space is driven to flow into the object space, through the outlet opening 215 in the ground electrode 213. When an appropriate voltage of some KV is applied to the discharge electrode 212 from the power supply, corona discharges occur between the negatively charged discharge electrode 212 and the ground electrode 213, and the gas passing near by the discharge electrode 212 ionizes negatively. By the way, simultaneously, a small amount of ozone can be generated, due to collision and dissociation between the negatively ionized oxygen molecule.

The cross section of the outlet opening 215 of the ground electrode 213 at the second position 219 in its downstream portion is smaller than that at the first position in its upstream portion. So, the velocity of the gas flow at the second position 219 in its downstream portion is larger than that at the first position 218 in its upstream portion. As a result, gas flow containing negative ion particles with high speed is supplied into the object space. Hence, the supplying rate of the negative ion particles per unit time can be increased, without increasing the consumption of electric power.

The corona discharges occur in the direction of a line, which links the discharge electrode 212 and the ground electrode 213 with the minimum length. This direction is substantially perpendicular to the gas flow direction. Thus, the number of the negative ion particles, which are caught by the ground electrode 213 and are not supplied into the object space, can be reduced.

The speed of the gas flow passing by the discharge electrode 212 is high, when as shown in the figure, the discharge electrode 212 is disposed in the outlet opening 215, in row with the second position 219 in the downstream portion of the outlet opening 215, where the cross section is smaller, or positioned at a downstream side of the second position 219. In such a configuration, not only the supply rate of negative ion particles into the object space but also generation rate of the negative ion particle increases. This is an advantage of this embodiment.

Especially, when the discharge electrode 212 is disposed in the outlet opening 215, being in row with the most downstream position 217, as shown in the figure, the generation rate of the negative ion particles becomes the maximum, and the number of the negative ion particles caught by the ground electrode 213 reaches the minimum, because the cross section of the gas flow is the minimum at the most downstream position 217, and the gas flow with the highest speed passes by the discharge electrode 212. Thus, this embodiment is very effective as a negative ion generating apparatus.

Moreover, if the shape of the outlet opening 215 of the ground electrode 213 is so formed, as shown in the figure, so that its longitudinal cross section decreases gradually from the most upstream position 216 to the most downstream position, the velocity of the gas flow increases smoothly, without suffering pressure loss of the gas flow. Thus the rate of obtaining the negative ion particles can be increased.

The form of the longitudinal cross section of the outlet opening 215 is not limited to a straight line, as shown in the figure. But also, it can be a line linked straight lines, parabola, arc, S-shaped curve etc.

The form of the transverse cross section of the outlet opening 215 is not limited to a circle, as shown in the figure. But also, it can be a triangle, square, polygons etc, so far as that its cross section at the second position 219 in the downstream portion is smaller than that at the first position 218 in the upstream portion, so as to increase the velocity of the gas flow at the second position 219.

The voltage to be applied to the discharge electrode 212 from the power supply 104 is determined, in principle, depending on the distance between the discharge electrode 212 and the ground electrode 213, i.e., gap distance. It is preferable to maintain the gap distance at an appropriate length, preferably about 10 cm. In this case, a voltage of about 8–10 KV is preferable as a voltage to be applied to the discharge electrode 212.

It is preferable that the structure of the discharge electrode 212 of this embodiment is composed of needle electrodes arranged angularly, as will be explained later. However, it is not limited in this structure. Any structure of discharge electrode is permissible, in so far as it has a shape applicable in a cylindrical ground electrode.

An oxygen containing gas, especially air, is preferable for the gas to be ionized, when this apparatus is for use of the prevention of bacteria propagation, air cleaning, deodorization etc, which are the specifically intended applications of the negative ion generating apparatus of the present invention. However, it is not limited to oxygen gas, and can be applied gases of sulfur hexafluoride, vapour, halogen etc.

As explained above, the present embodiment allows the increase of the supply rate of the negative ion particles into the object space, without increasing the consumption of electric power, because a high speed gas flow containing negative ion particles is provided into the object space. Further, it is possible to increase the generation rate of negative ion particles, because a high speed gas flow is ionized into negative ion at a position near to the discharge electrode. Moreover, it is possible to decrease the negative ion particles which are caught by the ground electrode and are not supplied into the object space, because the direction of the corona discharge is substantially perpendicular to the gas flow direction. Finally, it is possible to reduce the number of necessary parts the fabrication and to reduce the size of the apparatus, because the structure of the ground electrode functions as a gas flow controller.

Seventh Embodiment

The seventh embodiment relates to a structure of the discharge electrode, and is preferably applied to embodiments having a cylindrical ground electrode.

Figure 7A:
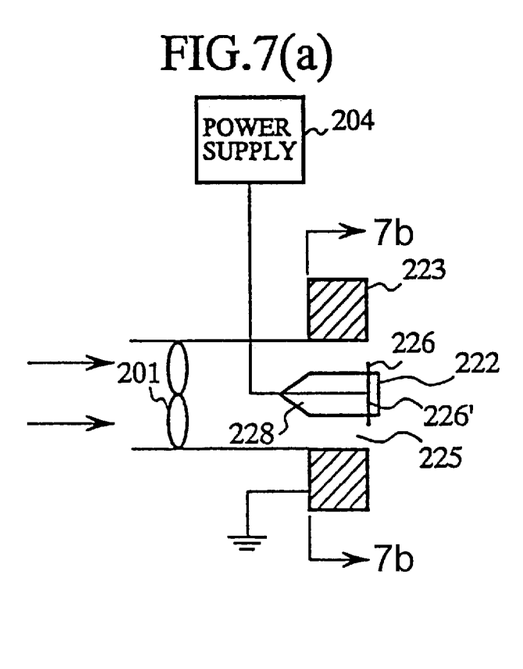
FIG. 7(a) shows a schematic cross section of the seventh embodiment of a negative ion generating apparatus according to the present invention along the flow direction.
Figure 7B:
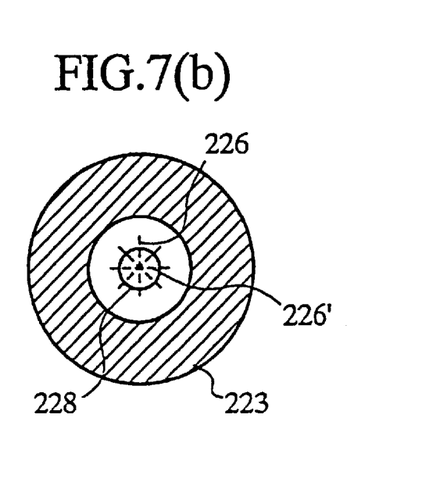
FIG. 7(b) shows a front view of the apparatus of FIG. 7(a) viewed in the direction 7b—7b of FIG. 7(a).

FIG. 7(a) shows a schematic cross section of the seventh embodiment of a negative ion generating apparatus according to the present invention along the flow direction, and FIG. 7(b) shows a front view of the apparatus of (a) viewed in the direction 7b—7b FIG. 7(a).

Reference numeral 201 denotes a ventilator, 222 is a discharge electrode (second electrode), 223 is a ground electrode having a cylindrical form surrounding the discharge electrode 222, 204 is a power supply, which applies negative voltage pulses of some KV to the discharge electrode 222, 225 is an outlet opening disposed in the ground electrode 223, which is a through hole along the axis of the cylinder, 226 is a needle electrode of the discharge electrode 222, 226' is an imbedded portion of the discharge electrode, 228 is a supporting member made from electrically insulating material, the transverse cross section of which is a circle.

The discharge electrode 222 is comprised of, preferably, a plurality of angularly arranged needle electrodes 226, which are projecting from a supporting member 228, and imbedded portions 206' of the needle electrodes 206, which are inwardly extended parts thereof and is imbedded in the supporting member 228. The supporting member is made from insulating material and is a circle in the transverse cross section,. The imbedded portions 106' are shown by broken lines in FIG. 7(b). The needle electrodes 226 are secured to be fixed at its specified angular position by the imbedded portions 106'. The imbedded portions 206' are connected to each other at a position in the supporting member, preferably at the center thereof, and further extends in the axial direction therefrom to the power supply 204. The supporting member is comprised of an upstream cone like portion and a downstream cylinder like portion.

The function of this embodiment is explained below.

In a similar manner as in the case of the sixth embodiment, external gas (preferably air) is taken in into the apparatus by the fan 201. The gas from the external space is driven to flow into the object space through the outlet opening 215 in the ground electrode 213. When an appropriate voltage of some KV is applied to the discharge electrode 212 from the power supply 204, corona discharges occur between the negatively charged discharge electrode 212 and the ground electrode 213, and the gas passing near by the discharge electrode 212 is ionized negatively.

In case that the needle electrodes 226 are angularly arranged, as shown in the figure, the distances between the tips of the adjacent needle electrodes can be made larger, compared to a case that needle electrodes are arranged in parallel to each other. Hence, it is possible to increase the number of the needle electrodes in a unit area, which corresponds to the number of sites where the corona discharges occur in a unit area, avoiding the mutual interference between the electric fields induced by the needle electrodes 226. As a result, the generation rate of the negative ion particles can be increased. Additionally, the cone like portion of the supporting member 228 functions not only to control the direction of the gas flow from the fan 201 to the outlet opening 225 but also to reduce the pressure loss of the gas flow. As a result, the velocity of the gas flow increases from the upstream towards the downstream.

It is preferable to arrange the needle electrodes 226 equidistantly in the angular direction, as shown in the figure, in order to increase the number of the needle electrodes in a unit area. For avoiding the mutual interference between the electric fields induced by the needle electrodes 226, it is preferable to design the distance between the tips of the needle electrodes and the length of the needle electrodes to be 10 mm and about 5 mm, respectively.

Regarding the functions of the supporting member 228 to control the direction of the gas, which flows from the fan 201 to the outlet opening 225, as well as to reduce the pressure loss therein, so as to increase the velocity of the flow from the upstream towards the downstream, it is sufficient to make larger the cross section of the supporting member 228 at its downstream portion than that at its upstream portion. The contour of the longitudinal cross section of the supporting member 228 is not limited to a shape of linked straight lines, as shown in the figure, but also a shape composed of a straight line, a parabola or an arc etc is permissible.

The appropriate voltage to apply to the discharge electrode 222 from the power supply 204, the distance between the needle electrode 226 and the ground electrode 223 (gap distance), the kind of gas applicable for gas to be ionized are the same as in the sixth embodiment.

The contour of the longitudinal cross section of the outlet opening 225 are not limited to a shape composed of a straight line, but also a parabola, an arc or an S-formed shape are permissible. The form of the transverse cross section of the outlet opening 225 is not limited to a circle, but also triangles, squares, or polygons are permissible, as is the case in the sixth embodiment. It is preferable to design the form of the transverse cross section of the supporting member 228 to correspond to that of the outlet opening 225, so as to make constant the gap distance and the needle length.

By increasing the number of the needle electrodes, avoiding the mutual interference between the needle electrodes 226, the generation rate of the negative ion particles can be increased. It is not always necessary to make smaller the cross section at the second position in the downstream portion of the outlet opening 225 than that at the first position in the upstream position thereof.

However, when the cross section at the second position in the downstream portion of the outlet opening 226 is smaller than that at the first position in the upstream portion thereof, the velocity of the gas flow passing by the needle electrodes 226 is large, as explained in the explanation of the sixth embodiment. Thus, the combination of the structure of the outlet opening and that of the needle electrodes is particularly effective for the proper functioning of the apparatus.

In such a case, it is preferable to arrange the needle electrodes 226 in row with the second position at the second position in the downstream portion in the outlet opening 225, where the cross section of the outlet opening is smaller, or to arrange it at the downstream side of the second position, and is the most preferable to arrange it in row with the most downstream position, where the cross section of the outlet opening is the minimum. This is the same as the case in the sixth embodiment.

As explained above, this embodiment allows to increase the number of the electrodes in a unit area, which corresponds to the number of sites where the corona discharges occur, and to increase the generation rate of negative ion particles, as well as to reduce the size of the apparatus. The discharge electrode is composed of needle electrodes having a free end, thus it is hard to be broken off. When the cross section of the supporting member at its downstream portion is larger than that at its upstream portion, it is possible to reduce the loss of pressure head in the gas flow, and to increase the velocity of the gas flow by the discharge electrodes, which leads to a further increase of generation rate of negative ion particles, as well as to control the direction of the gas flow.

Eighth Embodiment

This embodiment is a combination of the sixth embodiment and the seventh embodiment, and is one of the best modes of the present invention.

Figure 8A:
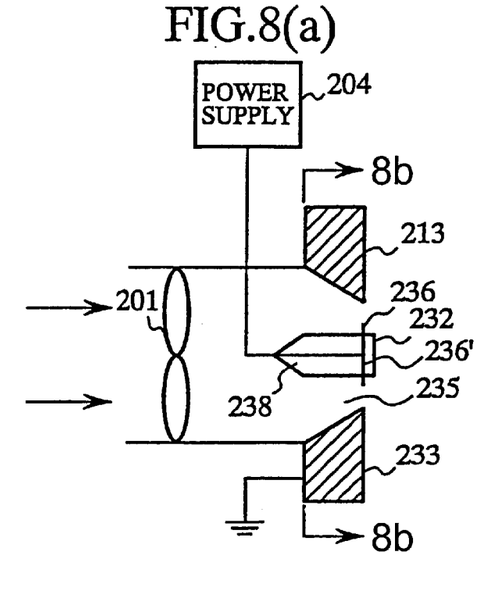
FIG. 8(a) shows a schematic cross section of the eighth embodiment of a negative ion generating apparatus according to the present invention along the flow direction.
Figure 8B:
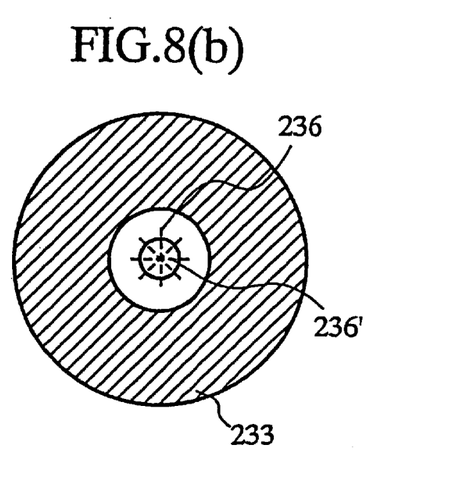
FIG. 8(b) shows a front view of the apparatus of (a) viewed in the direction 8b—8b of FIG. 8(a).

FIG. 8(a) shows a schematic cross section of the eighth embodiment of a negative ion generating apparatus according to the present invention, and FIG. 8(b) shows a front view of the apparatus of FIG. 8(a) viewed in the direction 8b—8b in FIG. 8(a).

Reference numeral 201 is a fan as a ventilator, 232 is a discharge electrode, 233 is a ground electrode formed in a cylindrical shape surrounding the discharge electrode 232, 204 is a power supply for applying a negative voltage pulses of some KV to the discharge electrode 232, 235 is an outlet opening disposed in the ground electrode 233, which is a through hole in the direction of the cylinder axis, 236 is needle electrode of the discharge electrodes 232, 236' is a embedded part of the discharge electrode, 238 is a supporting member made from insulating material, the cross section of which is a circle.

As is the case of the sixth embodiment, the longitudinal cross section of the outlet opening 235 decreases gradually from the most upstream position to the most downstream position, and the contour in this cross section is composed of straight lines. On the other hand, the contour of the transverse cross section is a circle. Thus, the velocity of the gas flow increases smoothly, without accompanying loss of pressure head in the gas flow, and the supplying rate of the negative ion particles into the object space can be increased.

The discharge electrodes 232 are arranged so as to be in row with the most downstream position of the outlet opening 235. The number of the negative ion particles, which are caught by the ground electrode, is suppressed into the minimum level by this structure. Moreover, the generation rate of the negative ion particles increases to the maximum level because the gas flow at highest velocity passes by the discharge electrode 232, As is the case of the seventh embodiment, the needle electrodes 236 of the discharge electrode 232 are arranged equidistantly in the angular direction so that the number of needle electrode in a unit area, which corresponds to the number of sites where the corona discharges occur, is maximized, while avoiding the mutual interference between electric fields of the needle electrodes 236. The maximum generation rate of the negative ion particles can be attained by this structure.

The discharge electrode 232 is comprised of needle electrodes 236, which are projecting from a cylinder formed portion of an electrically insulating supporting member 238 and are arranged in the angular direction, and their imbedded portions 236' inwardly extend into the supporting member 238 and are imbedded therein, which are shown by broken lines in FIG. 8(b). The imbedded portions assure to fix the arrangement of the needle electrodes.

Additionally, the supporting member 238 is comprised of a cone like portion at the upstream and a cylinder like portion at the downstream, this structure allows not only the control of the direction of the gas flow, which flows from the fan 201 to the outlet opening, but also reduces the loss of pressure head in the gas flow, and increases the velocity of the gas flow at the region near to the needle electrodes 236. Thus, the generation rate of the negative ion particles can be further increased.

As explained above, by this embodiment, it is possible to increase the generation rate and the supplying rate of the negative ion particles into the object space, as well as to make compact the size of the apparatus and to reduce the number of the necessary parts for the fabrication. Further, there are advantages that the discharge electrodes are not broken off, and that the direction of the gas flow can be controlled.

What is claimed is:

1. A negative ion generating apparatus comprising:
   a reaction chamber;
   a first electrode disposed within the reaction chamber;
   a second electrode disposed in the reaction chamber and spaced from the first electrode;
   a ventilator drawing gas from a gas inlet and directing the gas through the reaction chamber between the first electrode and the second electrode to generate a gas flow;
   a power supply to supply a voltage across the first electrode and the second electrode configured to induce a corona discharge between the first and second electrodes;
   an outlet opening for outlet of negative ion particles generated by the corona discharge in the reaction chamber; and
   an adjusting damper for narrowing a gas passage area, disposed in and functioning as a nozzle in the reaction chamber, the adjusting damper including a deflector having a first end pivotably connected to an inner surface of the reaction chamber and a freely rotatable second end, and a spring urging the deflector to narrow a gas passage area for controlling velocity of the gas flow, the first electrode being located adjacent to the second end of the deflector, and the second electrode being located closer to the outlet opening than the first electrode.

2. The negative ion generating apparatus according to claim 1, wherein the adjusting damper comprises a pair of plates facing each other along the gas flow.

3. The negative ion generating apparatus according to claim 1, comprising an object chamber in which objects to be exposed to the negative ion particles are disposed, the object chamber being connected with the outlet opening for the negative ion particles, and a negative ion particle density sensor in the object chamber detecting density of the negative ion particles supplied with ozone to the object chamber, and sending a negative ion particle density control signal to the ventilator through the power supply, the ventilator controlling gas flow in the apparatus in response to the negative ion particles density signal.

4. The negative ion generating apparatus according to claim 1, comprising an object chamber in which objects to be exposed to the negative ion particles are disposed, the object chamber being connected with the outlet opening for the negative ion particles, an ozone density sensor in the object chamber detecting density of ozone gas delivered with the negative ion particles to the object chamber, and a discharge controller receiving an ozone density control signal from the ozone density sensor and controlling the ozone density in response to the ozone density signal.

5. A negative ion generating apparatus comprising:
   a generally planar first electrode having an opening;
   a second electrode having an electrically insulating supporting member from which a plurality of needle electrodes disposed in a plane of the generally planar first electrode extend in radial directions, the second electrode being disposed in the opening of the first electrode and spaced from the first electrode;
   a ventilator drawing gas from an inlet and directing the gas through a space between the first electrode and the second electrode to generate a gas flow;
   a power supply to supply a voltage across the first electrode and the second electrode to induce a corona discharge between the first and second electrodes; and a substantially circular outlet opening for outlet of negative ion particles generated by the corona discharge in the gas between the first and second electrodes, wherein the second electrode is disposed within the circular outlet opening.

6. The negative ion generating apparatus according to claim 5, wherein the needle electrodes are arranged in the plane of the first electrode, equidistantly in angular direction.

7. The negative ion generating apparatus according to claim 5, wherein the supporting member has a circular cross-section.

8. The negative ion generating apparatus according to claim 5, wherein the supporting member has a larger cross-section closer to the circular outlet opening than closer to the ventilator.

* * * * *